(12) United States Patent
Deng et al.

(10) Patent No.: US 11,698,522 B2
(45) Date of Patent: Jul. 11, 2023

(54) SYSTEMS AND METHODS FOR CONNECTING A LIGHT CABLE TO AN ILLUMINATOR

(71) Applicant: Stryker Corporation, Kalamazoo, MI (US)

(72) Inventors: Wenjie Deng, San Jose, CA (US); Michelle Sun, San Jose, CA (US); Maziyar Keshtgar, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 196 days.

(21) Appl. No.: 17/191,501

(22) Filed: Mar. 3, 2021

(65) Prior Publication Data

US 2021/0278659 A1    Sep. 9, 2021

Related U.S. Application Data

(60) Provisional application No. 62/985,812, filed on Mar. 5, 2020.

(51) Int. Cl.
*G02B 6/42* (2006.01)
*G02B 23/24* (2006.01)
(Continued)

(52) U.S. Cl.
CPC ...... *G02B 23/2476* (2013.01); *A61B 1/00117* (2013.01); *A61B 1/0661* (2013.01); *F21V 21/088* (2013.01); *G02B 6/4204* (2013.01); *G02B 6/4292* (2013.01); *G02B 23/2461* (2013.01)

(58) Field of Classification Search
CPC . G02B 6/4292; G02B 6/0006; G02B 23/2476
See application file for complete search history.

(56) References Cited

U.S. PATENT DOCUMENTS 5,594,826 A * 1/1997 Wood ............... G02B 6/403
385/91
5,617,302 A * 4/1997 Kloots ............. G02B 6/3604
362/581

FOREIGN PATENT DOCUMENTS

EP    1530069 A1 *   5/2005   ........... G02B 6/4298

OTHER PUBLICATIONS

"Self-Centering Lens Mount—Standa". (Year: 2020).*
"Self Centering Lens Mounts—Global Analytical". (Year: 2018).*

* cited by examiner

*Primary Examiner* — Eric Wong
(74) *Attorney, Agent, or Firm* — Morrison & Foerster LLP

(57) ABSTRACT

An illuminator including a receptacle for connecting a light cable to an illuminator. The receptacle includes a clamp assembly having a plurality of clamping jaws that are moveable from an open configuration in which a connecter of the light cable can be positioned between the clamping jaws for receiving light traveling in a light pathway in the illuminator to a closed configuration in which the clamping jaws completely block the light pathway, and a clutch that is movable between an engaged position for holding the clamping jaws in the open configuration and a disengaged position for allowing the clamping jaws to move to a gripped configuration and to the closed configuration, the clutch can be pushed by the connector when the connector is positioned between the clamping jaws to move the clutch out of the engaged position so that the clamp assembly moves the clamping jaws to the gripped configuration.

39 Claims, 12 Drawing Sheets

(51) Int. Cl.
*A61B 1/06* (2006.01)
*F21V 21/088* (2006.01)
*A61B 1/00* (2006.01)

SYSTEMS AND METHODS FOR CONNECTING A LIGHT CABLE TO AN ILLUMINATOR

CROSS-REFERENCE TO RELATED APPLICATIONS

This application claims benefit of U.S. Provisional Application No. 62/985,812, filed Mar. 5, 2020, the contents of which is incorporated herein by reference in its entirety.

FIELD

This invention relates generally to illuminators, and more specifically, to devices and methods for providing illuminating light from an illuminator to an endoscope for endoscopic imaging.

BACKGROUND

In the medical field of endoscopy, illuminators are used to generate illuminating light for illuminating areas of interest that are located within the body of a patient. To guide the light from the illuminator to the area of interest, a light cable may be used. One end of the light cable is connected to a light outlet port of the illuminator and another end of the light cable is connected to an endoscope. During endoscopic imaging, the illuminator generates light that travels through the connected light cable, to the endoscope, and through the endoscope to the surgical cavity.

The light cable is generally removably connected to the illuminator so that the light cable can be cleaned and replaced when necessary. Because the light cable stretches across at least a portion of an operating theater from the illuminator to the endoscope in the sterile field, the light cable should be sufficiently secured to the illuminator to prevent inadvertent disconnection of the light cable from the illuminator. Inadvertent disconnection of the light cable from the illuminator can disrupt a medical procedure and can pose a safety hazard to operating room personnel since high powered light may escape from the illuminator.

SUMMARY

According to some embodiments, an illuminator includes a receptacle that securely connects a light cable to the illuminator and automatically shuts off a light pathway should the light cable be disconnected from the receptacle. The receptacle may include clamping jaws configured to grip onto a connector of the light cable. According to some embodiments, the positions of the clamping jaws are controlled by a locking guide. According to some embodiments, a clutch holds the locking guide in a position that holds the jaws open so that the connector of the light cable can be positioned between the clamping jaws. According to some embodiments, the clutch can be disengaged from the locking guide by the connector of the light cable. With the clutch disengaged, the locking guide moves the jaws to grip onto the connector positioned between the clamping jaws. According to some embodiments, the clamping jaws automatically close the clamping jaws to shut off the light pathway in the illuminator should the connector be removed from the grip of the clamping jaws.

According to some embodiments, an illuminator includes a receptacle for connecting a light cable to an illuminator, the receptacle includes a clamp assembly that includes a plurality of clamping jaws that are moveable by the clamp assembly from an open configuration in which a connecter of the light cable can be positioned between the clamping jaws for receiving light traveling in a light pathway in the illuminator to a closed configuration in which the clamping jaws completely block the light pathway; and a clutch that is movable between an engaged position in which the clutch engages the clamp assembly for holding the clamping jaws in the open configuration and a disengaged position in which the clutch is disengaged from the clamp assembly for allowing the clamping jaws to move to a gripped configuration in which the clamping jaws grip onto the connector positioned between the clamping jaws and to the closed configuration, the clutch including a central portion that can be pushed by the connector when the connector is positioned between the clamping jaws to move the clutch out of the engaged position so that the clamp assembly moves the clamping jaws to the gripped configuration.

In any of these embodiments, the clamp assembly may include a locking guide operatively connected to each clamping jaw of the plurality of clamping jaws, the locking guide configured for moving between a first position for holding the clamping jaws in the open configuration and a second position for holding the jaws in the closed configuration.

In any of these embodiments, clutch may be moved from the engaged position so that the locking guide moves the clamping jaws to the gripped configuration.

In any of these embodiments, the clutch may be configured to move translationally between the engaged position and the disengaged position in a direction orthogonal to a movement of the locking guide between the first position and the second position.

In any of these embodiments, the clutch in the engaged position may hold the locking guide in the first position and the clutch in the disengaged position may be disengaged from the locking guide to allow the locking guide to move to the second position and to a third position.

In any of these embodiments, the locking guide may include rolling pins configured to interface the clutch for reducing friction during clutch movement between the engaged position and the disengaged position with the locking guide.

In any of these embodiments, each clamping jaw of the plurality of clamping jaws may include at least one protrusion that slideably engages the locking guide for operatively connecting each clamping jaw of the plurality of clamping jaws to the locking guide.

In any of these embodiments, the receptacle may include a user-operated actuator operatively connected to the locking guide for moving the locking guide from the second position to the first position.

In any of these embodiments, the locking guide may be configured to automatically move the clamping jaws to the closed configuration when the gripped connector is removed from between the clamping jaws.

In any of these embodiments, the locking guide may be moveable to a third position for holding the clamping jaws in the gripped configuration.

In any of these embodiments, the illuminator may include a base plate, wherein the clamping jaws and the locking guide are positioned on a first side of the base plate and the clutch is positioned on a second side of the base plate that is opposite the first side of the base plate.

In any of these embodiments, the locking guide may be spring loaded via a spring that attaches the locking guide to a base plate via machined hooks in the base plate.

In any of these embodiments, the locking guide may be spring loaded via a spring that attaches the locking guide to a base plate via machined apertures in the base plate.

In any of these embodiments, the locking guide may be spring loaded via a spring that attaches the locking guide to a base plate via machined hooks in the locking guide.

In any of these embodiments, the locking guide may be spring loaded via a spring that attaches the locking guide to a base plate via machined apertures in the locking guide.

In any of these embodiments, each clamping jaw of the plurality of clamping jaws may be rotationally moveable between the open configuration, the gripped configuration, and the closed configuration by the locking guide.

In any of these embodiments, the locking guide may be rotationally moveable between the first position, the second position, and a third position, the third position configured for holding the clamping jaws in the gripped configuration.

In any of these embodiments, the receptacle may include a user-operated actuator operatively connected to the clamp assembly for moving the clamping jaws from the closed configuration to the open configuration.

In any of these embodiments, each clamping jaw of the plurality of clamping jaws may include a recessed portion adjacent to an overlapping portion so that in the closed configuration, the overlapping portion of each clamping jaw extends over the recessed portion of at least another clamping jaw of the plurality of clamping jaws.

In any of these embodiments, the illuminator may include a base plate that includes a first side and a second side opposite to the first side, wherein a plurality of protrusions of the clutch extend from the second side of the base plate to the first side of the base plate when the clutch is in the engaged position.

In any of these embodiments, the illuminator may include a locking guide, wherein the clutch holds the locking guide in a first position and wherein a disengaged position in which the clutch is disengaged from the locking guide allows the locking guide to move to a second position and to a third position.

In any of these embodiments, the plurality of clamping jaws may include a plurality of inwardly facing gripping surfaces that are outwardly spaced from the central portion of the clutch when the clutch is in the engaged position.

In any of these embodiments, the central portion of the clutch may extend between the plurality of clamping jaws when the clutch is in the engaged position.

In any of these embodiments, the clutch may be configured to move translationally between the engaged position and the disengaged position in a direction orthogonal to a movement of the plurality of clamping jaws between the open configuration and the closed configuration.

In any of these embodiments, the illuminator may include a base plate, wherein the clamp assembly is positioned on a first side of the base plate and the clutch is positioned on a second side of the base plate that is opposite the first side of the base plate.

In any of these embodiments, the clutch may include a plurality of protrusions that extend between the second side of the base plate and the first side of the base plate for holding the locking guide in the first position.

In any of these embodiments, the illuminator may include a base plate for supporting the receptacle, wherein the central portion of the clutch fits into an aperture in the base plate.

In any of these embodiments, the receptacle may be configured to receive connectors having a range of diameters.

In any of these embodiments, the connector of the light cable may be for an endoscope.

In any of these embodiments, the illuminator may be configured to provide illuminating light to an endoscope via the light cable.

In any of these embodiments, the illuminator may include the light cable.

In any of these embodiments, the illuminator may include a lens for focusing light travelling in the light pathway to the central portion of the clutch.

In any of these embodiments, the illuminator may include a light pipe located in the central portion of the clutch.

In any of these embodiments, the central portion of the clutch may extend between an aperture of a base plate when the clutch is in the engaged position and in the disengaged position.

In any of these embodiments, the illuminator may include one or more guide posts that support the clutch between a back plate and a base plate.

In any of these embodiments, the clutch may include rolling pins configured to interface the one or more guide posts for reducing friction during clutch movement between the engaged position and the disengaged position with the clamp assembly.

In any of these embodiments, the one or more guide posts may include a hard stop that limits clutch movement between the engaged position and the disengaged position with the clamp assembly.

According to some embodiments, an illuminator includes a receptacle for connecting a light cable to an illuminator, the receptacle includes a plurality of clamping jaws; and a locking guide operatively connected to each clamping jaw of the plurality of clamping jaws and configured for moving between a first position for holding the clamping jaws in an open configuration in which a connecter of the light cable can be positioned between the clamping jaws for receiving light traveling in a light pathway in the illuminator and a second position for holding the clamping jaws in a closed configuration in which the clamping jaws completely block the light pathway.

In any of these embodiments, each clamping jaw of the plurality of clamping jaws may include at least one protrusion that slideably engages the locking guide for operatively connecting each clamping jaw of the plurality of clamping jaws to the locking guide.

In any of these embodiments, the clamping jaws may be moveable to a gripped configuration in which the clamping jaws grip onto the connector positioned between the clamping jaws.

In any of these embodiments, each clamping jaw of the plurality of clamping jaws may include a recessed portion adjacent to an overlapping portion so that in the closed configuration, the overlapping portion of each clamping jaw extends over the recessed portion of at least another clamping jaw of the plurality of clamping jaws.

In any of these embodiments, the receptacle may include a user-operated actuator operatively connected to the locking guide for moving the locking guide from the second position to the first position.

In any of these embodiments, the locking guide may be configured to automatically move the clamping jaws to the closed configuration when the gripped connector is removed from between the clamping jaws.

In any of these embodiments, the locking guide may be moveable to a third position for holding the clamping jaws in a gripped configuration in which the clamping jaws grip onto the connector positioned between the clamping jaws.

In any of these embodiments, the illuminator may include a clutch that is movable between an engaged position in which the clutch holds the locking guide in the first position and a disengaged position in which the clutch is disengaged from the locking guide for allowing the locking guide to move to the second position and to a third position, wherein the locking guide in the third position holds the clamping jaws in a gripped configuration in which the clamping jaws grip onto the connector positioned between the clamping jaws.

In any of these embodiments, the locking guide may include rolling pins configured to interface the clutch for reducing friction during clutch movement between the engaged position and the disengaged position with the locking guide.

In any of these embodiments, the illuminator may include a lens for focusing light travelling in the light pathway to a central portion of the clutch.

In any of these embodiments, the illuminator may include a light pipe located in a central portion of the clutch.

In any of these embodiments, a central portion of the clutch may extend between an aperture of a base plate when the clutch is in the engaged position and in the disengaged position.

In any of these embodiments, a central portion of the clutch may be pushed by the connector when the connector is positioned between the clamping jaws to move the clutch out of the engaged position so that the locking guide moves the clamping jaws to the gripped configuration.

In any of these embodiments, the clutch may be configured to move translationally between the engaged position and the disengaged position in a direction orthogonal to a movement of the plurality of jaws between the open configuration and the closed configuration and to a movement of the locking guide between the first position and the second position.

In any of these embodiments, a central portion of the clutch may extend between the plurality of clamping jaws when the clutch is in the engaged position.

In any of these embodiments, the illuminator may include a base plate, wherein the clamping jaws and the locking guide are positioned on a first side of the base plate and the clutch is positioned on a second side of the base plate that is opposite the first side of the base plate.

In any of these embodiments, the illuminator may include a base plate for supporting the receptacle, wherein a central portion of the clutch fits into an aperture in the base plate.

In any of these embodiments, the illuminator may include a base plate that includes a first side and a second side opposite to the first side, wherein a plurality of protrusions of the clutch extend from the second side of the base plate to the first side of the base plate when the clutch is in the engaged position for holding the locking guide in the first position.

In any of these embodiments, the plurality of clamping jaws may include a plurality of inwardly facing gripping surfaces that are outwardly spaced from the central portion of the clutch when the plurality of protrusions of the clutch engage the locking guide for holding the locking guide in the first position.

In any of these embodiments, the illuminator may include one or more guide posts that support the clutch between a back plate and a base plate.

In any of these embodiments, the clutch may include rolling pins configured to interface the one or more guide posts for reducing friction during clutch movement between the engaged position and the disengaged position with the locking guide.

In any of these embodiments, the one or more guide posts may include a hard stop that limits clutch movement between the engaged position and the disengaged position with the locking guide.

In any of these embodiments, the receptacle may be configured to receive connectors having a range of diameters.

In any of these embodiments, the connector of the light cable may be for an endoscope.

In any of these embodiments, the illuminator may be configured to provide illuminating light to an endoscope via the light cable.

In any of these embodiments, the illuminator may include the light cable.

In any of these embodiments, the illuminator may include a clutch that is movable between an engaged position with the clamp assembly for holding the clamping jaws in the open configuration and a disengaged position in which the clutch is disengaged from the clamp assembly for allowing the clamping jaws to move to the gripped configuration and to the closed configuration.

In any of these embodiments, the locking guide may be spring loaded via a spring that attaches the locking guide to a base plate via machined hooks in the base plate.

In any of these embodiments, the locking guide may be spring loaded via a spring that attaches the locking guide to a base plate via machined apertures in the base plate.

In any of these embodiments, the locking guide may be spring loaded via a spring that attaches the locking guide to a base plate via machined hooks in the locking guide.

In any of these embodiments, the locking guide may be spring loaded via a spring that attaches the locking guide to a base plate via machined apertures in the locking guide.

According to some embodiments, an illuminator includes a receptacle for connecting a light cable to an illuminator, the receptacle includes a plurality of clamping jaws that are moveable from an open configuration in which a connecter of the light cable can be positioned between the jaws for receiving light traveling in a light pathway in the illuminator to a closed configuration in which the clamping jaws completely block the light pathway; a locking guide operatively connected to the plurality of clamping jaws for moving the plurality of clamping jaws between the open configuration and the closed configuration, the locking guide being moveable between a first position configured for holding the clamping jaws in the open configuration, a second position configured for holding the clamping jaws in the closed configuration, and a third position configured for holding the clamping jaws in a gripped configuration in which the clamping jaws grip onto the connector positioned between the clamping jaws; and a clutch that is movable between an engaged position for holding the locking guide in the first position and a disengaged position for allowing the locking guide to move to the second position and to the third position, the clutch comprising a central portion that can be pushed by the connector when the connector is positioned between the jaws to move the clutch out of the engaged position so that the locking guide moves the clamping jaws to the gripped configuration, wherein the locking guide is configured to automatically move the clamping jaws to the closed configuration when the gripped connector is removed from between the clamping jaws.

In any of these embodiments, each clamping jaw of the plurality of clamping jaws may include a recessed portion adjacent to an overlapping portion so that in the closed configuration, the overlapping portion of each clamping jaw extends over the recessed portion of at least another clamping jaw of the plurality of clamping jaws.

In any of these embodiments, each clamping jaw of the plurality of clamping jaws may be rotationally moveable between the open configuration, the gripped configuration, and the closed configuration by the locking guide.

In any of these embodiments, the locking guide may be rotationally moveable between the first position, the second position, and the third position.

In any of these embodiments, the receptacle may be configured to receive connectors having a range of diameters.

In any of these embodiments, the illuminator may include a base plate that includes a first side and a second side opposite to the first side, wherein a plurality of protrusions of the clutch extend from the second side of the base plate to the first side of the base plate when the clutch is in the engaged position.

In any of these embodiments, the central portion of the clutch may extend between the plurality of clamping jaws when the clutch is in the engaged position.

In any of these embodiments, the plurality of clamping jaws may include a plurality of inwardly facing gripping surfaces that are outwardly spaced from the central portion of the clutch when the clutch is in the engaged position.

In any of these embodiments, the clutch may be configured to move translationally between the engaged position and the disengaged position in a direction orthogonal to a movement of the plurality of clamping jaws between the open configuration and the closed configuration.

In any of these embodiments, the illuminator may include a base plate, wherein the plurality of clamping jaws and the locking guide are positioned on a first side of the base plate and the clutch is positioned on a second side of the base plate that is opposite the first side of the base plate.

In any of these embodiments, the illuminator may include a base plate for supporting the receptacle, wherein the central portion of the clutch fits into an aperture in the base plate.

In any of these embodiments, the illuminator may include a lens for focusing light travelling in the light pathway to the central portion of the clutch.

In any of these embodiments, the illuminator may include a light pipe located in the central portion of the clutch.

In any of these embodiments, the connector of the light cable may be for an endoscope.

In any of these embodiments, the locking guide may include rolling pins configured to interface the clutch for reducing friction during clutch movement between the engaged position and the disengaged position with the locking guide.

In any of these embodiments, the locking guide may spring loaded via a spring that attaches the locking guide to a base plate via machined hooks in the base plate.

In any of these embodiments, the locking guide may be spring loaded via a spring that attaches the locking guide to a base plate via machined apertures in the base plate.

In any of these embodiments, the locking guide may be spring loaded via a spring that attaches the locking guide to a base plate via machined hooks in the locking guide.

In any of these embodiments, the locking guide may be spring loaded via a spring that attaches the locking guide to a base plate via machined apertures in the locking guide.

In any of these embodiments, the illuminator may include one or more guide posts that support the clutch between a back plate and a base plate.

In any of these embodiments, the clutch may include rolling pins configured to interface the one or more guide posts for reducing friction during clutch movement between the engaged position and the disengaged position with the locking guide.

In any of these embodiments, the one or more guide posts may include a hard stop that limits clutch movement between the engaged position and the disengaged position with the locking guide.

According to some embodiments, an illuminator includes a receptacle for connecting a light cable to an illuminator, a method for connecting the receptacle to the light cable includes using a locking guide in a first position to hold a plurality of clamping jaws in an open configuration, wherein the locking guide is operatively connected to each clamping jaw of the plurality of clamping jaws; holding the locking guide in the first position via a clutch engaged with the locking guide; positioning a connector of the light cable between the clamping jaws in the open configuration; pushing the connector positioned between the jaws against a central portion of the clutch to disengage the clutch from the locking guide; gripping the inserted connector positioned between the clamping jaws; and automatically moving the clamping jaws to the closed configuration in response to removing the gripped connector from between the clamping jaws.

In any of these embodiments, gripping the inserted connector positioned between the clamping jaws may include moving the clamping jaws to a gripped configuration.

In any of these embodiments, automatically moving the clamping jaws may include automatically moving the locking guide to a second position that holds the clamping jaws in the closed configuration.

In any of these embodiments, automatically moving the clamping jaws may include maintaining the clutch in the disengaged position.

In any of these embodiments, gripping the inserted connector may include moving the locking guide from the first position in which the locking guide holds the clamping jaws in the open configuration to a second position in which the locking guide holds the clamping jaws in the gripped configuration.

BRIEF DESCRIPTION OF THE FIGURES

The invention will now be described, by way of example only, with reference to the accompanying drawings, in which.

DETAILED DESCRIPTION

Figure 1:
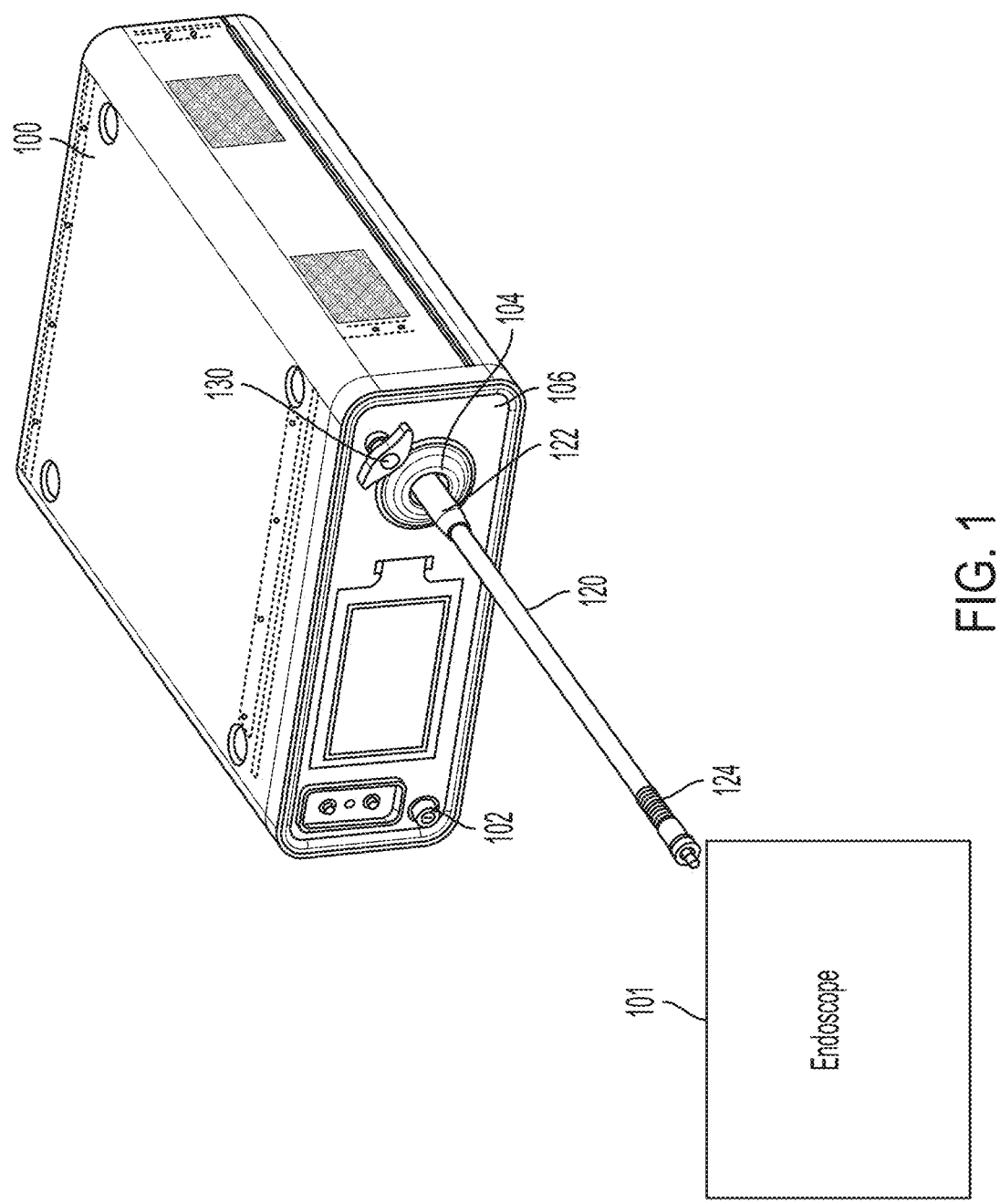
FIG. 1 shows an endoscopic imaging system that includes an illuminator according to some embodiments.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Disclosed herein, according to various embodiments, are systems and methods for securely connecting a light cable to a receptacle of an illuminator and automatically blocking the light pathway through the receptacle when the connector is disconnected from the illuminator. According to some embodiments, the receptacle includes a plurality of clamping jaws that can clamp onto a connector of the light cable and close shut to block the light pathway when the connector is removed. The clamping jaws may include an open configuration in which the light cable may be positioned between the clamping jaws, a gripped configuration in which the inserted light cable is gripped by the clamping jaws and light can travel from the illuminator to the light cable, and a closed configuration in which the clamping jaws block light from exiting the receptacle. According to some embodiments, the clamping jaws can automatically move from the gripped configuration to the closed configuration should the gripped light cable be removed from the grip of the clamping jaws.

According to some embodiments, to achieve the various clamping jaw configurations, the receptacle may include a locking guide that is moveable and operatively connected to each clamping jaw of the plurality of clamping jaws such that movement of the locking guide moves the clamping jaws in unison. According to some embodiments, different positions of the locking guide correspond to the different configurations for the clamping jaws. For example, the locking guide may be rotationally moveable between a first position for holding the clamping jaws in the open configuration, a second position for holding the clamping jaws in the gripped configuration, and a third position for holding the clamping jaws in the closed configuration. Being operatively connected to the clamping jaws, movement of the locking guide from the first position to the second position and then to the third position respectively moves the clamping jaws from the open configuration to the gripped configuration and to the closed configuration. According to some embodiments, the locking guide may be spring loaded to urge the locking guide towards the third position for holding the clamping jaws closed.

According to some embodiments, the receptacle may include a clutch that engages the locking guide to hold the locking guide in the first position for holding the clamping jaws open. According to some embodiments, the clutch may be disengaged from the locking guide to allow the locking guide to move away from the first position. According to some embodiments, the clutch may be disengaged from the locking guide via a translational movement that is orthogonal to a direction of movement of the clamping jaws. The clutch may be translated away from engagement with the locking guide by pushing the connector of the light cable into the receptacle. According to some embodiments, as a result of pushing the clutch with the connector, the clutch releases the locking guide from the first position. The released locking guide is then urged by the spring toward the second position, which moves the clamping jaws to the gripped configuration. In the gripped configuration, gripping surfaces of the clamping jaws grip onto the connecter positioned between the jaws. According to some embodiments, when the connector of the light cable is subsequently pulled out of the grip of the clamping jaws, the locking guide moves from the second position to the third position which moves the clamping jaws from the gripped configuration to the closed configuration.

According to some embodiments, the clamping jaws may rotationally move between the open configuration, the gripped configuration, and the closed configuration. According to some embodiments, the receptacle may include a base plate onto which each clamping jaw of the plurality of clamping jaws is rotationally pinned. During movement between clamping jaw configurations, each clamping jaw may rotate about a pivot point at which the respective clamping jaw is rotationally pinned to the base plate.

According to some embodiments, each clamping jaw of the plurality of clamping jaws may include an inwardly facing gripping surface for gripping the connector positioned between the clamping jaws. In the open configuration, these gripping surfaces may be spaced from each other to allow the connector to be positioned between the clamping jaws. According to some embodiments, the open configuration of the clamping jaws may accommodate connectors having a range of sizes such that gripping surfaces of the clamping jaws securely grip onto an outer surface of connectors of various sizes.

According to some embodiments, in the closed configuration, each clamping jaw of the plurality of clamping jaws may interface with at least one other clamping jaw of the plurality clamping jaws to prevent light from escaping the illuminator through the clamping jaws. According to some embodiments, the plurality of clamping jaws may include overlapping portions for blocking light in the closed configuration. According to some embodiments, each clamping jaw has a portion that overlaps a recessed shape of another clamping jaw in the closed configuration. The overlapping portions minimize light leakage as the gripping surfaces may wear out from gripping connectors.

According to some embodiments, rolling pins, low friction coatings, low friction bushing, ball bearings, or roller bearings, or any combination thereof may be used to ease movement of the locking guide between the first position for holding the clamping jaws open, the second position for holding the clamping jaws gripped around the connector, and the third position for holding the clamping jaws closed. According to some embodiments, rolling pins are preferred and are more cost effective and feasible to manufacture compared to low friction coatings, low friction bushing, ball bearings, or roller bearings. According to some embodiments, the locking guide may include one or more sets of rolling pins to ease movement of the locking guide between the first position for holding the clamping jaws open, the second position for holding the clamping jaws gripped around the connector, and the third position for holding the clamping jaws closed. According to some embodiments, the rolling pins reduce frictional forces associated with movement of the locking guide. According to some embodiments, the rolling pins may reduce friction associated with a force loaded on the locking guide by a spring. According the some embodiments, the rolling pins may be positioned in different orientations with respect to the locking guide.

According to some embodiments, rolling pins of the locking guide may reduce frictional forces associated with movement of the clutch. According to some embodiments, rolling pins may interface with the clutch to reduce friction between the clutch and the locking guide during translational movement of the clutch.

According to some embodiments, movement of a user-operated actuator operatively connected to the locking guide moves the locking guide such that the clamping jaws move between different configurations. According to some embodiments, the user-operated actuator may move the locking guide from the second position in which the jaws grip the connector towards the first position in which the jaws are held open for removing the light cable from the receptacle. The user-operated actuator may also move the locking guide from the third position in which the jaws are held closed to the first position in which the jaws are held open for preparing the receptacle to receive a connector between the clamping jaws.

According to some embodiments, the locking guide may be mounted onto the base plate and may be operatively connected to a spring that urges the locking guide towards the third position in which the locking guide holds the jaws closed. The spring may include loops at opposite ends of the spring such that one loop attaches to the base plate and the other loop attaches to the locking guide. According to some embodiments, one loop of the spring may wrap around a machined aperture in the base plate and the other loop of the spring may wrap around a machined aperture in the locking guide. According to some embodiments, one loop of the spring may wrap around a machined hook in the base plate and the other loop of the spring may wrap around a machined hook in the locking guide. According to some embodiments, one loop of the spring may be attached to a machined aperture, while the other loop of the spring may be attached to a machined hook.

According to some embodiments, a central portion of the clutch extends between the clamping jaws in the open configuration such that the central portion can be translationally moved by the connector positioned between the clamping jaws. According to some embodiments, the clutch may be translated away from engagement with the locking guide when the central portion of the clutch is pushed by the connector inserted into the receptacle. According to some embodiments, in the open configuration, inwardly facing gripping surfaces of the clamping jaw may be outwardly spaced from an outer surface of the central portion of the clutch such that when the connecter moves the central portion away from engagement with the locking guide, the inwardly facing gripping surfaces grip onto the connector.

According to some embodiments, the central portion of the clutch may allow light to travel through the clutch and to the connector of the light cable positioned between the clamping jaws. According to some embodiments, the central portion of the clutch may be positioned about a light pipe for passing light to the connector of the light cable. According to some embodiments, the light pipe extends between the central portion of the clutch and the clutch translationally moves about the light pipe within the central portion of the clutch. According to some embodiments, the central portion of the clutch may include a lens for focusing light travelling within the illuminator onto the connector without requiring a light pipe.

According to some embodiments, the clutch may include a plurality of protrusions for engaging the locking guide such that the plurality of protrusions hold the locking guide in the first position that holds the jaws open. According to some embodiments, the plurality of protrusions of the clutch engage the locking guide by extending between the base plate on which the clutch is mounted and at least between a portion of the locking guide. The clutch may be disengaged from the locking guide such that the plurality of protrusions of the clutch extend between the base plate, but do not extend between the locking guide. Thus, the disengaged clutch releases the locking guide to move between the second position in which the clamping jaws grip onto the connector and the third position in which the clamping jaws are held closed.

According to some embodiments, the protrusions of the clutch may press against a bottom surface of the locking guide or the base plate to prevent the clutch from engaging the locking guide when the inserted cable is removed. According to some embodiments, the protrusions of the clutch may press against a bottom surface of the locking guide or the base plate to prevent the clutch from moving the clamping jaws from the gripped configuration to the open configuration when the inserted cable is removed.

According to some embodiments, the receptacle may include guide posts that extend between the base plate and a back plate for supporting the clutch. According to some embodiments, the back plate may be part of an enclosure that includes at least one or more light sources for generating light. According to some embodiments, springs are located about a portion of the guide posts for urging the clutch towards the base plate.

According to some embodiments, the clutch may include rolling pins to reduce the friction of the translational clutch movement between engagement and disengagement with the locking guide. The rolling pins may be positioned such that the longitudinal axis of the pins are perpendicular to the translational movement of the clutch. The rolling pins may interface with guide posts such that as the clutch moves along a longitudinal axis of the guide posts, the pins roll about a direction perpendicular to the longitudinal axis of the guide posts, thereby reducing friction of the clutch movement.

According to some embodiments, the guide posts may include protrusions as hard stops for limiting the translational movement of the clutch. According to some embodiments, the hard stops limit the translational movement of the clutch such that the central portion is prevented from pressing against and damaging the glass light pipe during translational movement of the clutch.

According to some embodiments, the plurality of clamping jaws and the locking guide may be mounted on a first side of the base plate and the clutch may be mounted on a second side of the base plate. According to some embodiments, the clutch may extend from the second side of the base plate to the first side of the base plate. According to some embodiments, the clutch may extend from the second side of the base plate such that the clutch crosses the first side of the base plate.

According to some embodiments, the receptacle can receive connectors having an outer surface with a diameter of at least 0.05 inches, at least 0.10 inches, at least 0.15 inches, at least 0.20 inches, at least 0.25 inches, or at least 0.30 inches. According to some embodiments, the receptacle can receive connectors having an outer surface with a diameter of at most 0.30 inches, at most 0.35 inches, at most 0.40 inches, at most 0.45 inches, at most 0.50 inches, at most 1 inch.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

In addition, it is also to be understood that the singular forms "a", "an," and "the" used in the following description are intended to include the plural forms as well, unless the context clearly indicates otherwise. It is also to be understood that the term "and/or," as used herein, refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

Figure 12:
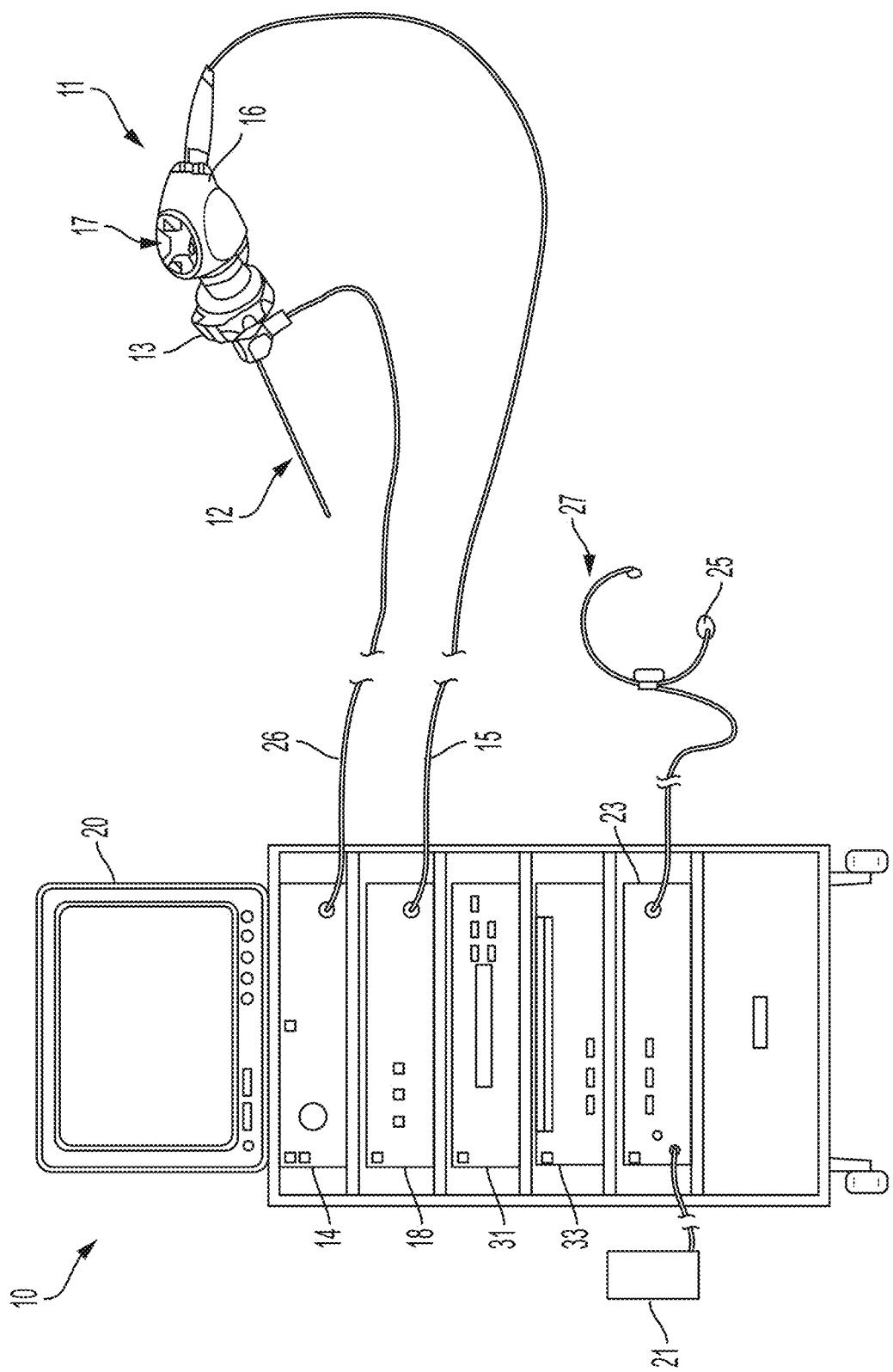
FIG. 12 shows an endoscopic imaging system according to some embodiments.

FIG. 1 shows an illuminator 100, according to some embodiments, for an endoscopic imaging system (such as endoscopic imaging system 10 of FIG. 12). The illuminator 100 may include a power switch 102 to power on the illuminator to generate light that may travel through a receptacle 104 of the illuminator 100. A light cable 120 may be connected to the receptacle 104 of the illuminator 100 so that light generated by the illuminator 100 can be directed to an endoscope 101. For example, a first end 122 of the light cable 120 may be connected to receptacle 104 of the illuminator 100 and a second end 124 of the light cable 120 may be attached, for example, to the endoscope 101. The receptacle 104 may be configured to grip onto the light cable 120 that is inserted within the receptacle 104 and may automatically close shut to block the light pathway when the light cable 120 is removed from the receptacle 104. A user-operated actuator 130 may extend through a user interface 106 of the illuminator 100 for allowing manual operation of the receptacle 104 for inserting the light cable 120 or for removing the light cable 120 from the receptacle 104.

Figure 2:
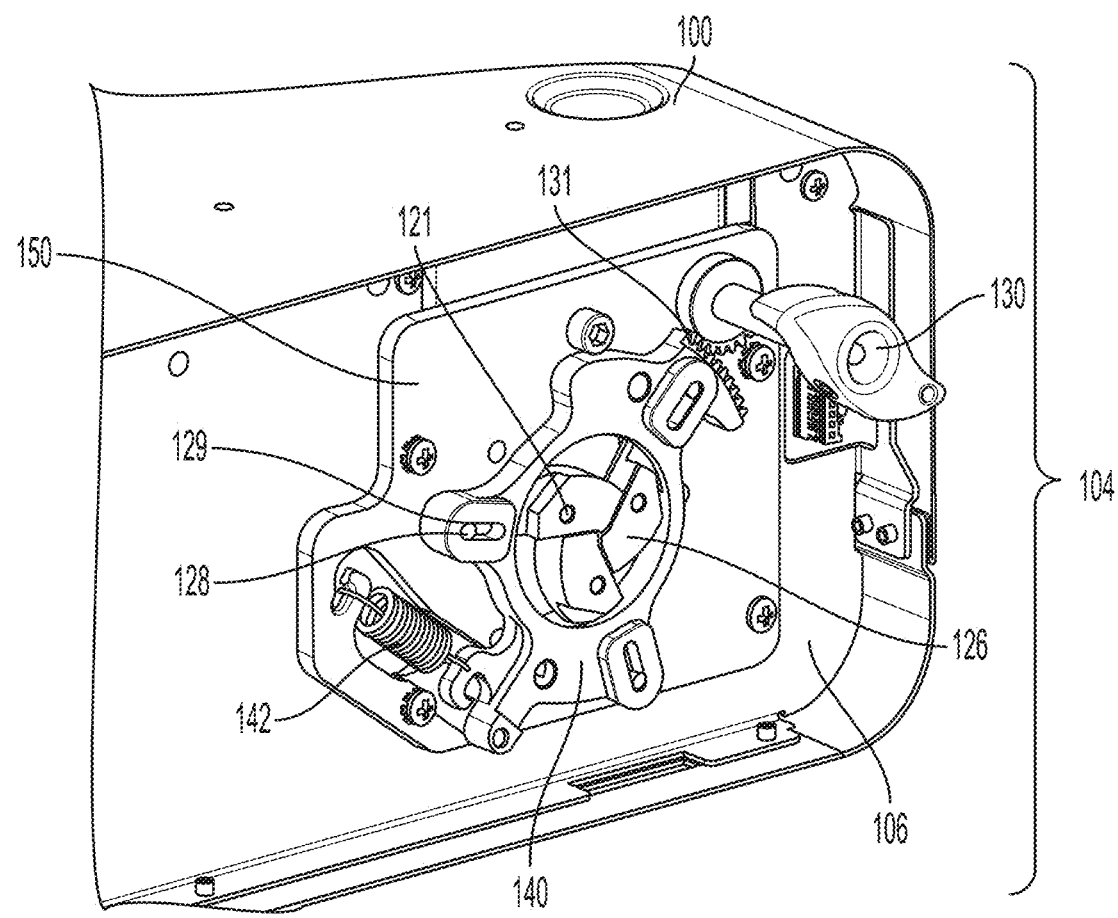
FIG. 2 shows a receptacle of an illuminator according to some embodiments.

FIG. 2 shows the receptacle 104 of illuminator 100, according to some embodiments. The receptacle 104 may include a plurality of clamping jaws 126 configured to grip onto a connector (such as first end 122) of a light cable (such as light cable 120) inserted into the receptacle 104 and configured to automatically close to block the light pathway when the connector of the light cable is removed from the receptacle 104. The receptacle 104 of FIG. 2 is shown with the clamping jaws 126 in a closed configuration. According to some embodiments, in the closed configuration, the plurality of clamping jaws 126 can completely block light traveling in the illuminator from passing through the clamping jaws 126. The clamping jaws 126 may be held in the closed configuration by a locking guide 140. The locking guide 140 may be operatively connected to each of the clamping jaws 126 such that when the locking guide 140 moves or remains stationary, the clamping jaws 126 respectively move or remain stationary. According to some embodiments, each clamping jaw of the plurality of clamping jaws is operatively connected to the locking guide 140 via at least one protrusion 128 that may slide within slots 129 of the locking guide 140. According to some embodiments, the locking guide 140 may be spring loaded to urge the clamping jaws towards the closed configuration. For example, spring 142 can urge the locking guide 140 towards a position that holds the clamping jaws 126 closed. According to some embodiments, each clamping jaw is rotationally pinned to a base plate 150 at a pivot point 121 such that each clamping jaw 126 may rotate about its respective pivot point 121.

According to some embodiments, the receptacle may include a user-operated actuator 130 operatively connected to the locking guide 140 such that the user may move the user-operated actuator 130 to move the locking guide 140 to change the configuration of the clamping jaws 126. According to some embodiments, the user-operated actuator 130 may be operatively connected to the locking guide 140 via interlocking gear teeth 131. According to some embodiments, the user-operated actuator 130, together with the locking guide 140, may be configured to overcome a spring force by the spring 142 when the user-operated actuator 130 is actuated by a user. According to some embodiments, overcoming the spring force of the spring 142 allows the locking guide 140 to move such that the clamping jaws are no longer held closed by the locking guide 140.

Figure 3B:
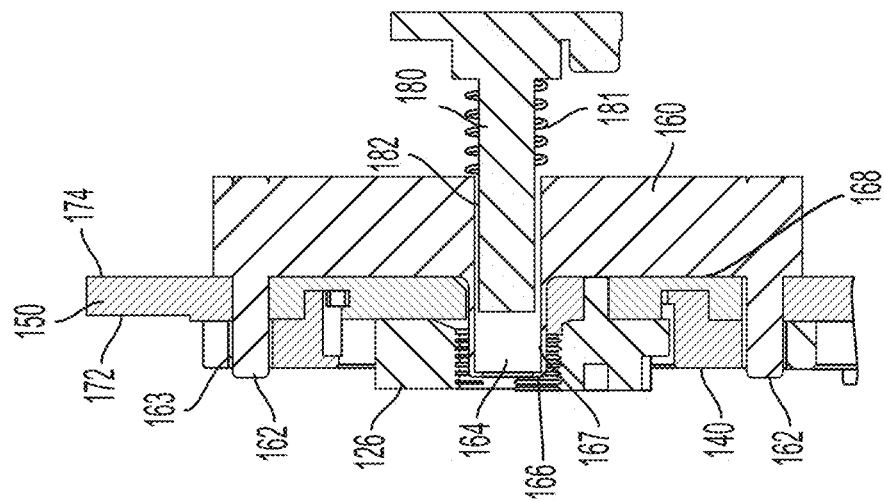
FIGS. 3A and 3B show the clamping jaws of the receptacle of FIG. 2 in an open configuration according to some embodiments.
Figure 3A:
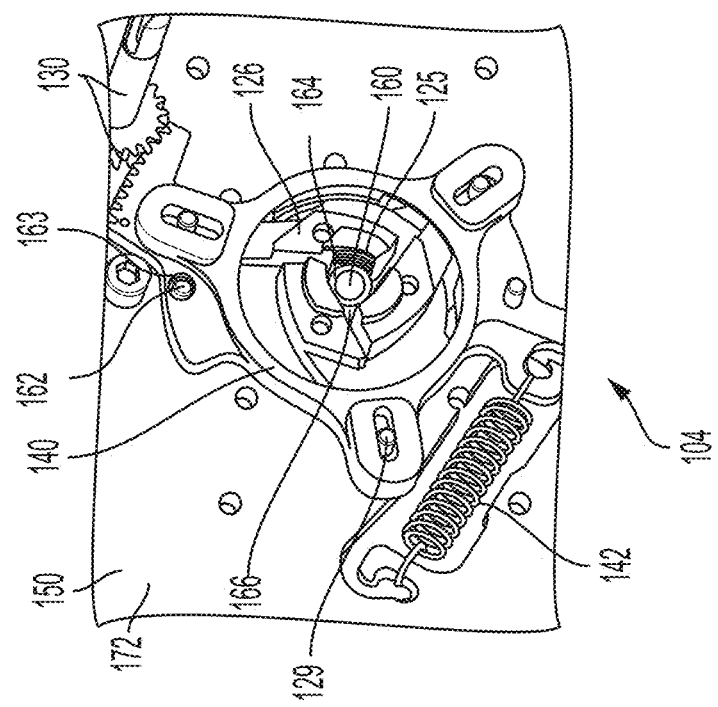

FIGS. 3A and 3B show a front view and cross-sectional view, respectively, of receptacle 104 in which the clamping jaws 126 are in an open configuration, according to some embodiments. With the jaws 126 in the open configuration, a light cable (such as light cable 120 of FIG. 1) can be positioned within the clamping jaws 126 such that light generated by the illuminator may be received by the light cable, for example via a light pipe 180 which directs light generated by one or more light sources (not shown) of the illuminator.

According to some embodiments, the receptacle 104 includes a moveable clutch 160 that engages the locking guide 140 to hold the locking guide 140 in a first position that holds the clamping jaws 126 open. According to some embodiments, the engagement of the clutch 160 with the locking guide 140 holds the locking guide 140 in the first position such that the clutch 160 resists the spring force of the spring connected to the locking guide 140 that urges the locking guide 140 towards a position in which the clamping jaws 126 are closed.

According to some embodiments the plurality of clamping jaws 126 and the locking guide 140 may be mounted on a first side 172 of the base plate 150 and the moveable clutch 160 may be mounted on a second side 174 of the base plate 150 such that the clutch 160 is movable between the first side 172 and the second side 174 of the base plate 150 for engaging or disengaging with the locking guide 140. According to some embodiments, the clutch 160 may extend from the second side 174 of the base plate 150 such that the clutch 160 crosses the first side 172 of the base plate 150 for engaging the locking guide 140. According to some embodiments, the clutch 160 may include a plurality of protrusions 162 that extend between the base plate 150 and between slots 163 of the locking guide 140 for securing the rotatably moveable locking guide 140 in the first position that holds the clamping jaws 126 in the open configuration. As shown in the embodiment of FIG. 3A, the plurality of protrusions 162 may be a plurality of pins.

According to some embodiments, a central portion 164 of the clutch 160 may extend through the base plate 150 and between the clamping jaws 126 such that the central portion 164 is accessible to the connector (such as connector 122) of the light cable. According to some embodiments, the central portion 164 of the clutch 160 may extend between the plurality of clamping jaws 126 such that gripping surfaces 125 of the clamping jaws 126 are spaced from an outer surface 166 of the central portion 164 of the clutch 160.

According to some embodiments, the light pipe 180 may be located in the central portion 164 of the clutch 160 for passing light to the connector (such as connector 122) of the light cable. According to some embodiments, the central portion 164 of the clutch 160 may be positioned about the light pipe 180 for passing light to the connector of the light cable. According to some embodiments, the clutch 160 may move relative to the light pipe 180. According to some embodiments, an inner surface 167 of the central portion 164 is outwardly spaced from an outer surface 182 of the light pipe 180 to prevent damaging the light pipe 180 during movement of the clutch 160.

According to some embodiments, the clutch 160 may be translated away from engagement with the locking guide 140 when the central portion 164 of the clutch 160 is pushed by the connector of the light cable (such as first end 122 of light cable 120) as the connector is inserted into the receptacle 104. According to some embodiments, pushing the central portion 164 of the clutch 160, compresses a spring 181 configured to urge the clutch 160 towards the base plate 150. The spring 181 may be positioned about a portion of the light pipe 180 such that in a compressed state of the spring 181, the clutch 160 does not engage the locking guide 140. According to some embodiments, as a result of pushing the central portion 164 with the connector and compressing the spring 181 with the clutch 160, the plurality of protrusions 162 are removed from between the slots 163 of the locking guide 140. With the plurality of protrusions 162 no longer extending between the slots 163 of the locking guide, the clutch 160 releases the locking guide 140 from the first position. According to some embodiments, the released locking guide 140 is then urged by the spring 142 toward a second position for allowing the clamping jaws 126 to move to a gripped configuration (as shown, for example, in FIG. 4) in which the inserted light cable 120 is gripped by the clamping jaws 126 and light can travel from the illuminator to the light cable.

According to some embodiments, the receptacle 104 may include guide posts 175 that extend between the base plate 150 and a back plate 168 to support the clutch 160 and its translational movement associated with engagement and disengagement with the locking guide 140. According to some embodiments, the back plate 168 may be part of an enclosure 169 that includes at least one or more light sources (not shown) for generating light. According to some embodiments, springs 171 located about a portion of the guide posts 175 urge the clutch 160 towards the base plate 150 to engage the clutch 160 with the locking guide 140. Springs 171 may be configured similar to spring 181 of FIG. 3B, which has been described previously. Thus, for simplicity, springs 171 will not be described in detail.

According to some embodiments, the guide posts 175 may include shoulders 173 as hard stops for limiting the translational movement of the clutch 160 during disengagement of the clutch 160 from the locking guide 140. The hard stops 173 prevent the inner surface 167 of the central portion 164 from damaging the glass light pipe 180 by preventing the inner surface 167 from pressing against the glass light pipe 180 during translational movement of the clutch 160.

According to some embodiments, the protrusions 162 of the clutch 160 prevent the clutch 160 from engaging the locking guide 140 when the gripped connector 122 is removed. According to some embodiments, the protrusions 162 of the clutch 160 may press against a bottom surface of the locking guide 140 or the second side 174 of the base plate 150 to prevent the clutch 160 from engaging the locking guide 140 which also prevents the locking guide 140 from moving the clamping jaws 126 from the gripped configuration to the open configuration when the inserted cable 120 is removed. According to some embodiments, pressing the protrusions 162 against a bottom surface of the locking guide 140 of the second side 174 of the base plate when the clutch is disengaged minimizes wear of the central portion 164 and clamping jaws 126.

According to some embodiments, the clutch remains disengaged with the locking guide 140 when the gripped connector 122 is removed from between clamping jaws 126. The removal of the gripped connector 122 and continued disengagement of clutch 160 allows the spring 142 to move the locking guide 140 from the second position to the third position for holding the jaws closed. FIGS. 5A and 5B show the clamping jaws 126 of receptacle 104 in the closed configuration according to some embodiments. The locking guide 140 may be operatively connected to the plurality of clamping jaws 126 such that movement of the locking guide 140 from the second position to the third position moves the clamping jaws 126 from the gripped configuration to the closed configuration. According to some embodiments, the locking guide 140 may be held in the third position via spring 142. For example, the spring 142 (as shown in FIG. 5B) may be in a more compressed state (compared to spring 142 of FIG. 4 and spring 142 of FIG. 3A) to hold the locking guide 140 in the third position.

According to some embodiments, the plurality of clamping jaws 126 may include overlapping portions for minimizing light leakage in the closed configuration as the gripping surfaces may wear out from gripping connectors. According to some embodiments, the overlapping portions may be positioned between a bottom surface 132 of the clamping jaws 126 and the gripping surfaces 125 of the clamping jaws 126. According to some embodiments, each clamping jaw of the plurality of clamping jaws 126 may have a recessed shape that accommodates an extended portion of at least one other clamping jaw such that in the closed configuration, the extended portion of each clamping jaw overlaps the recessed shape of another clamping jaw 126.

Figure 4:
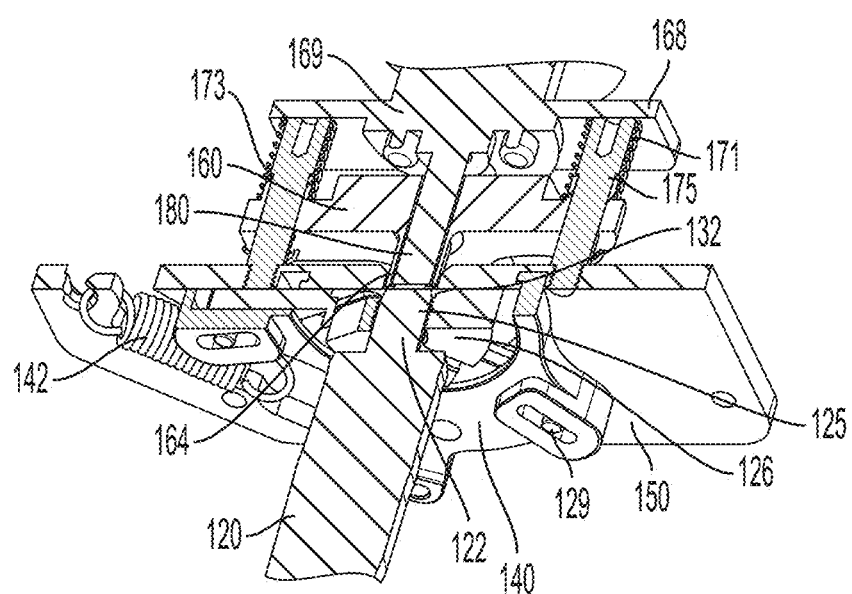
FIG. 4 shows a cross-sectional view of the clamping jaws of the receptacle of FIG. 2 in a gripped configuration according to some embodiments.
Figure 5A:
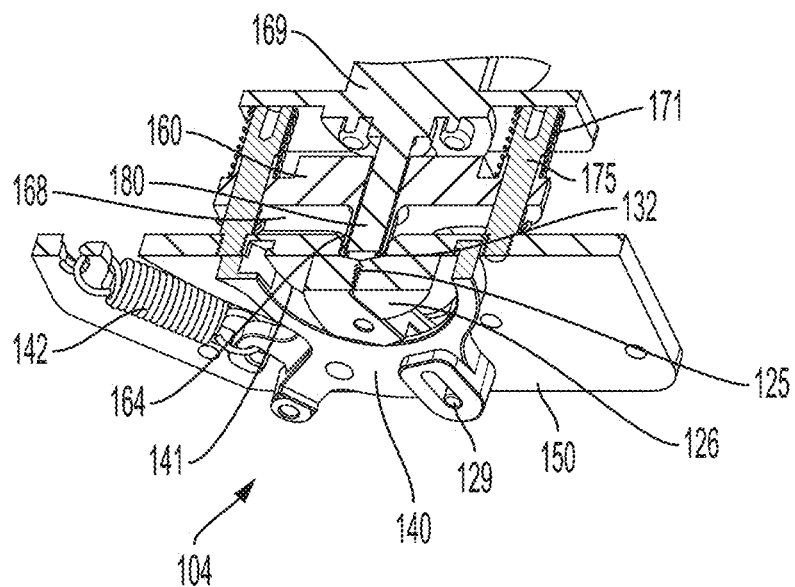
FIGS. 5A and 5B show the clamping jaws of the receptacle of FIG. 2 in a closed configuration according to some embodiments.
Figure 5B:
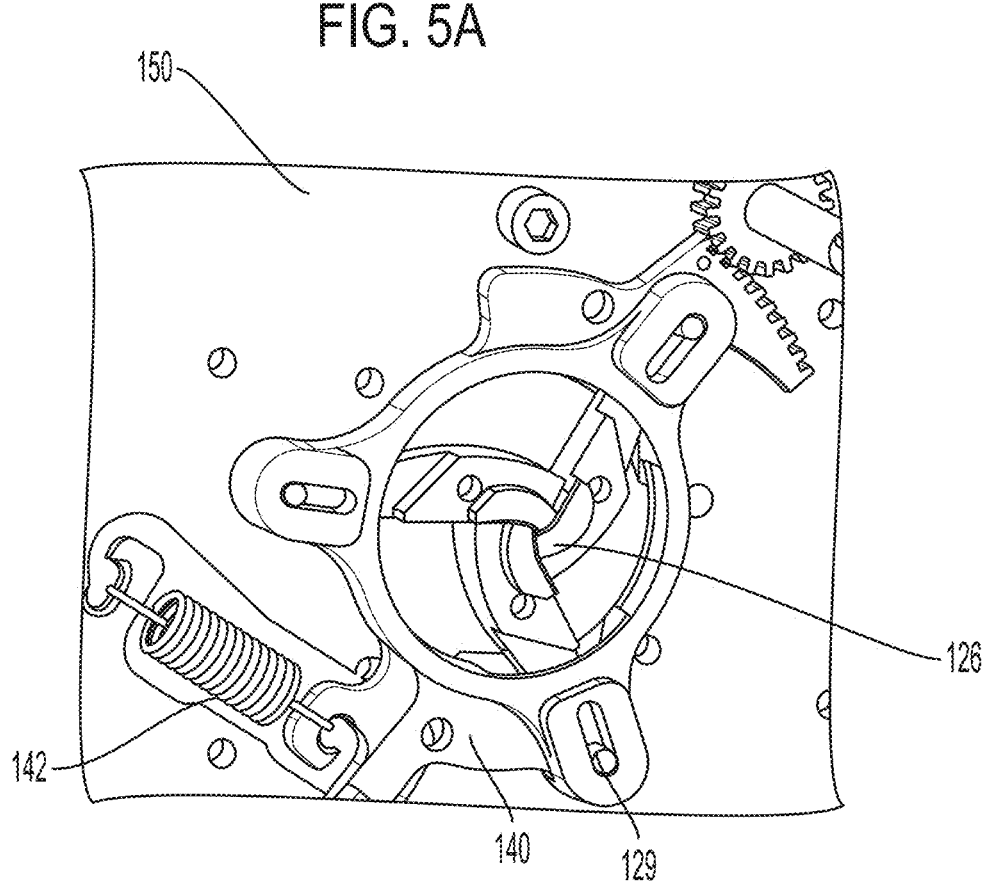

According to some embodiments, clamping jaws 126 may rotationally move between the open configuration (for example, as shown in FIG. 3), the gripped configuration (for example, as shown in FIG. 4), and the closed configuration (for example, as shown in FIG. 5). During movement between clamping jaw configurations, each clamping jaw may rotate about the point 121 at which the respective clamping jaw is rotationally pinned.

Figure 6B:
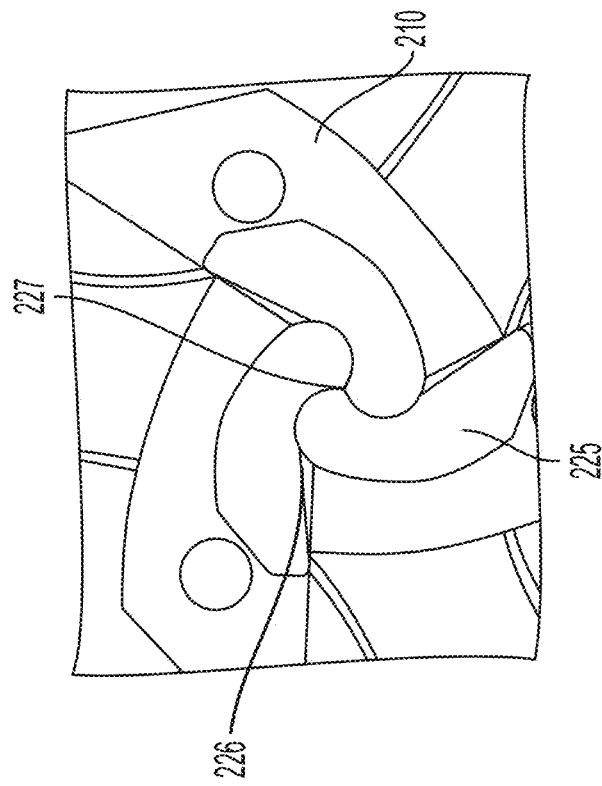
FIGS. 6A and 6B show the clamping jaws of a receptacle of an illuminator according to some embodiments.
Figure 6A:
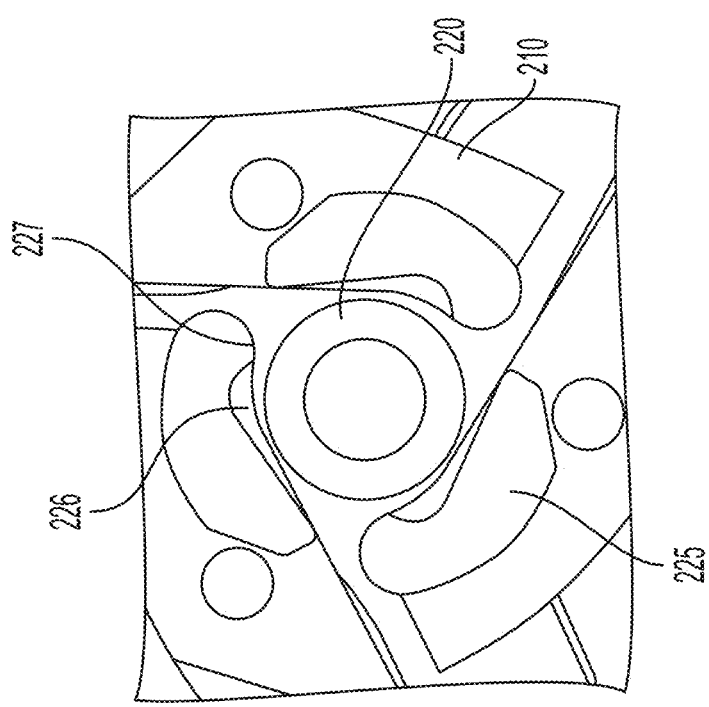

FIGS. 6A and 6B show an exemplary plurality of clamping jaws 210 for gripping onto a connector (such as connector 122) of a light cable (such as light cable 120) and for automatically shutting off a light pathway from an illuminator (such as illuminator 100). The clamping jaw 210 may be used in receptacles such as receptacle 104. According to some embodiments, the plurality of clamping jaws 210 may include overlapping portions on a top face 225 of the jaws for minimizing light leakage in the closed configuration as the gripping surfaces may wear out from gripping connectors. According to some embodiments, each clamping jaw of the plurality of clamping jaws 210 may have a recessed shape 226 that accommodates an extended portion 227 of at least one other clamping jaw such that in the closed configuration, the extended portion 227 of each clamping jaw overlaps the recessed shape 226 of another clamping jaw 126 to block the light pathway through the receptacle.

FIG. 6A shows the plurality of clamping jaws 210 that include extended portions 227 and recessed shapes 226 in the open configuration according to some embodiments. In the open configuration, a central portion 220 of the clutch is accessible to a connector (such as connecter 122) positioned between the clamping jaws 210. FIG. 6B shows the plurality of clamping jaws 210 that include extended portions 227 and recessed shapes 226 in the closed configuration.

Figure 7:
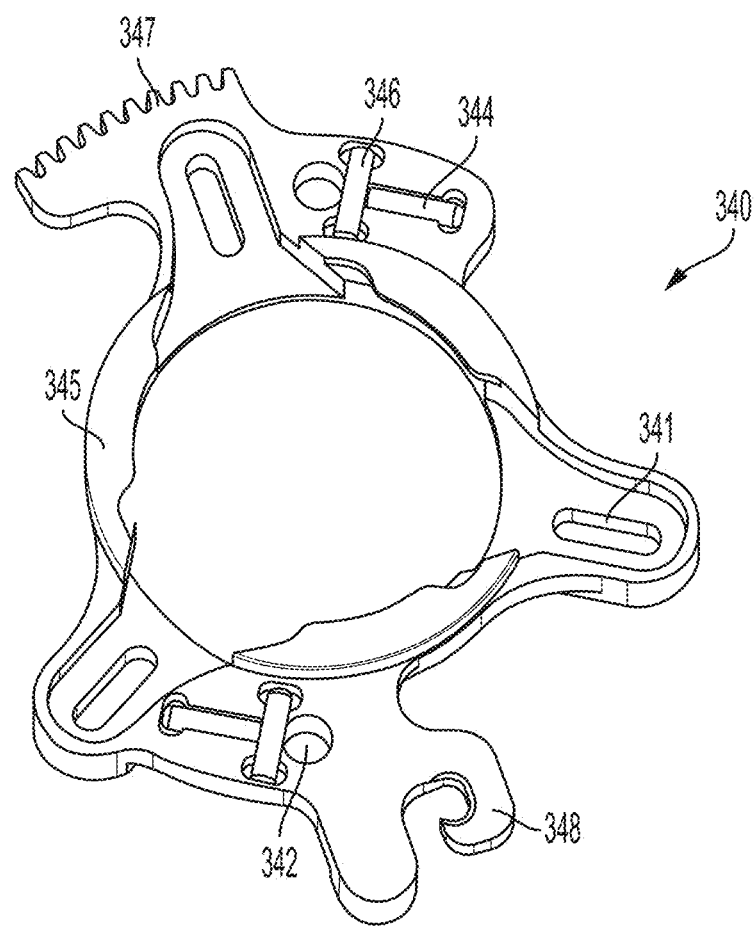
FIG. 7 shows the locking guide of a receptacle of an illuminator according to some embodiments.

FIG. 7 shows an exemplary locking guide 340 for guiding movement of a plurality of clamping jaws (such as clamping jaws 126, 210). The locking guide 340 may be used, for example, for receptacles such as receptacle 104. The locking guide 340 may be shaped 345 such that the locking guide 340 is operatively connected to each clamping jaw of a plurality of clamping jaws (such as clamping jaws 126, 210). The locking guide 340 may include slots 341 (such as slots 129), apertures 342 (such as 163), and gear teeth 3467(such as gear teeth 131) as previously described.

According to some embodiments, the locking guide 340 may include one or more sets of rolling pins 344, 346 to ease movement of the locking guide 340 between a first position for holding the clamping jaws open, a second position for holding the clamping jaws gripped around the connector, and a third position for holding the clamping jaws closed. According to some embodiments, the rolling pins 344, 346 reduce frictional forces associated with movement of the locking guide 340. According to some embodiments, the rolling pins 344, 346 may reduce friction associated with a force loaded on the locking guide by a spring (such as spring 142). According the some embodiments, the rolling pins 344, 346 may be positioned in different orientations with respect to the locking guide 340.

According to some embodiments, the one or more sets of rolling pins 344, 346 of the locking guide 340 may be configured to reduce frictional forces associated with movement of a clutch (such as clutch 160). According to some embodiments, rolling pins 346 may be configured to interface with a plurality of protrusions (such as protrusions 162) of a clutch (such as clutch 160) to reduce friction between the clutch and the locking guide 340 during translational movement of the clutch. According to some embodiments, the rolling pins 346 may be configured to rotate in a rotational direction that is orthogonal to a translational direction of movement of the clutch. According to some embodiments, an outer surface of the rolling pins 346 may be configured to interface an outer surface of the plurality of protrusions (such as protrusions 162) of the clutch (such as clutch 160) for reducing friction between the clutch and locking guide 340. According to some embodiments, the rolling pins 346 may be positioned adjacent to apertures 342 such that an outer surface of the rolling pins 346 forms at least part of the apertures 342.

According to some embodiments, the rolling pins 344, 346 may be cylindrical or spherical and may be configured in one or more directions with respect to the locking guide 340 to reduce friction as the clutch (such as 160) engages and disengages the locking guide 340. A first rolling pin 346 may be cylindrical and oriented with its longitudinal axis aligned with a radial direction of the ring-shaped portion 345. The radial direction, for example, may extend from a center point of the locking guide 340 (which may also be the center point of the ring-shaped portion 345) towards the ring-shaped portion 345 of the locking guide 340. A second rolling pin 344 may be cylindrical and oriented with its longitudinal axis aligned with a tangential direction of the ring-shaped portion 345 of the locking guide 340. According to some embodiments, the locking guide 340 may include a first set of rolling pins that includes a plurality of rolling pins 346 and a second set of rolling pins that includes a plurality of rolling pins 344 that are oriented in a different direction with respect to the locking guide 340 than rolling pins 346. According to some embodiments, the first set of rolling pins may have a different shape from the second set of rolling pins. According to some embodiments, one rolling pin of the first set of rolling pins may be adjacent to one rolling pin of the second set of rolling pins.

Figure 8B:
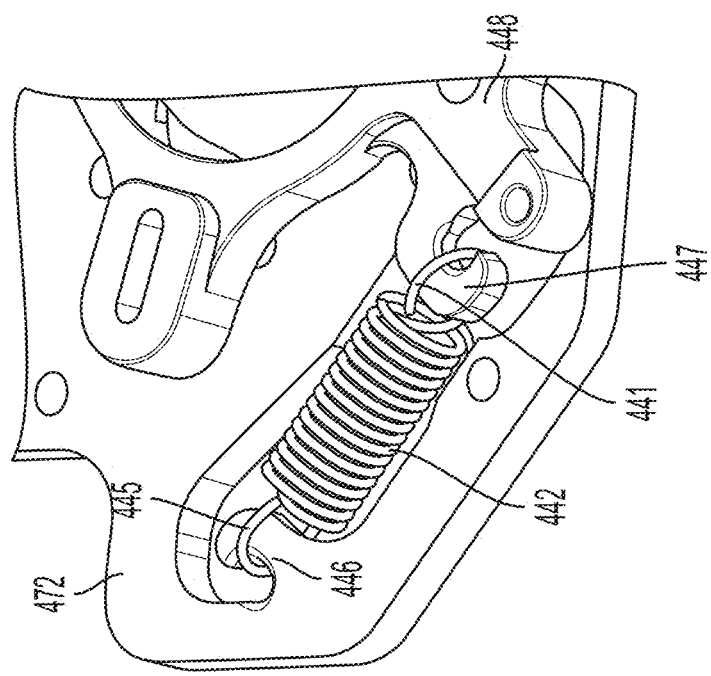
FIGS. 8A and 8B show spring-loaded locking guides of a receptacle according to some embodiments.
Figure 8A:
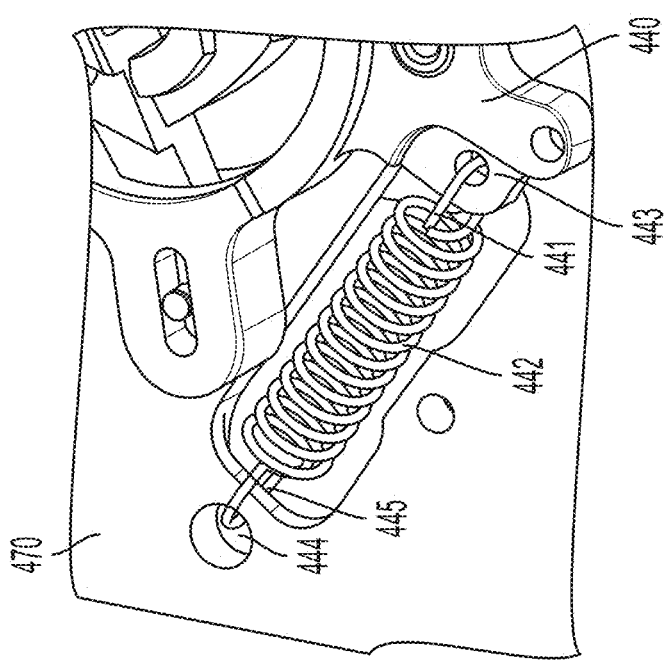

FIGS. 8A and 8B show examples of spring-loaded locking guides for urging the locking guides towards a position, according to some embodiments, that may be used in receptacles such as receptacle 104. FIG. 8A shows that a spring 442 of the spring-loaded locking guide 440 may be attached to a base plate 470 and the locking guide 440 by machined apertures 444, 443 according to some embodiments. According to some embodiments, the spring 442 may include loops on both ends. A first end 445 of the spring 442 may loop around a machined aperture 444 in the base plate 470. A second end 441 of the spring 442 may loop around a machined aperture 443 in the locking guide 470.

FIG. 8B shows that the spring 442 of the spring-loaded locking guide 448 may be attached to a base plate 472 and the locking guide 448 by machined loops 446, 447. According to some embodiments, the first end 445 of the spring 442 may loop around a machined hook 446 in the base plate 472. According to some embodiments, the second end 441 of the spring 442 may loop around a machined hook 447 in the locking guide 448. According to some embodiments, one end of the spring may loop around a machined aperture and the other end of the spring may loop around a machined hook.

Figure 9:
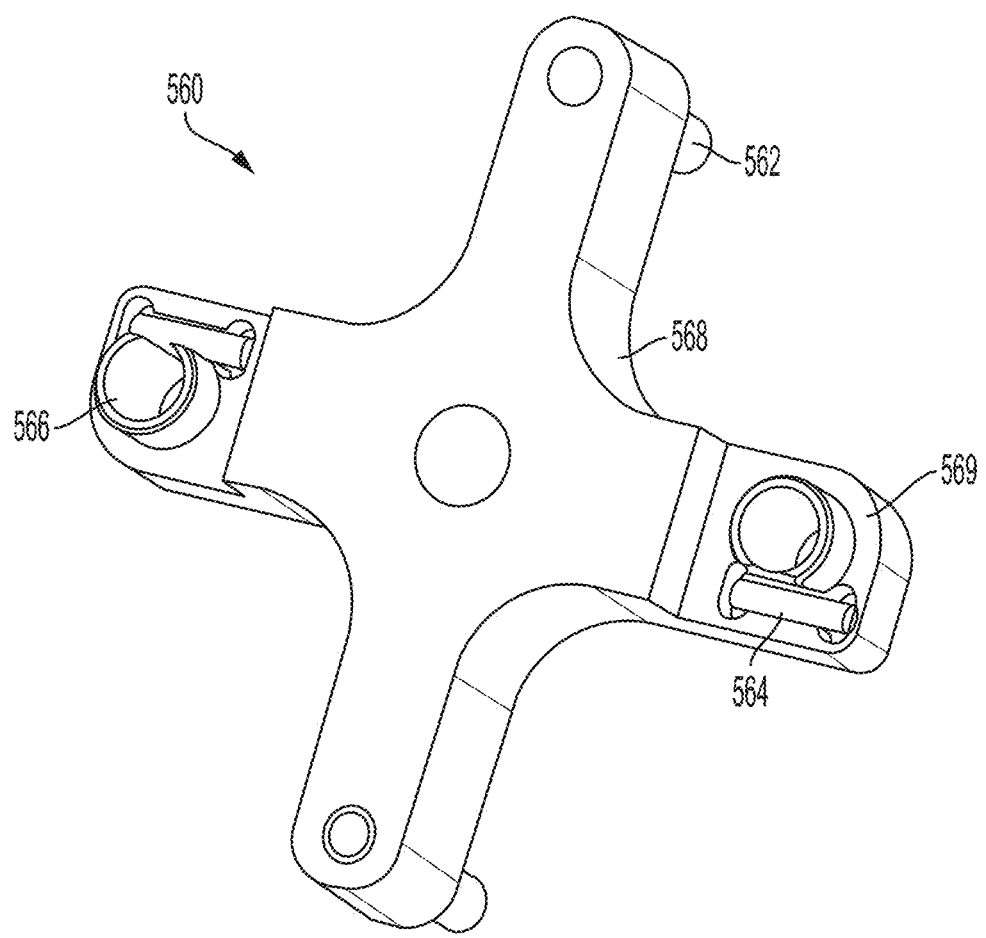
FIG. 9 shows a clutch of a receptacle according to some embodiments.

FIG. 9 shows an example of a clutch 560 for engaging a locking guide (such as locking guide 140), according to some embodiments. The clutch 560 may be used for receptacles such as receptacle 104. According to some embodiments, the clutch 560 may include rolling pins 564 to reduce the friction between the clutch 160 and guide posts (for example, guide posts 175) as the clutch 160 moves between engagement and disengagement with the locking guide (for example, such as locking guide 140). According to some embodiments, the rolling pins 564 may be positioned such that a longitudinal axis of the pins 564 are perpendicular to the translation movement of the clutch 560. The rolling pins may interface with the guide posts (such as guide posts 175) that extend between guide frames 566 to support clutch 560. According to some embodiments, the rolling pins 564 may be positioned on a second side 569 of the clutch opposite to a first side 568 of the clutch in which a plurality of protrusions 562 extend to engage a locking guide (for example, such as locking guide 140).

Figure 10:
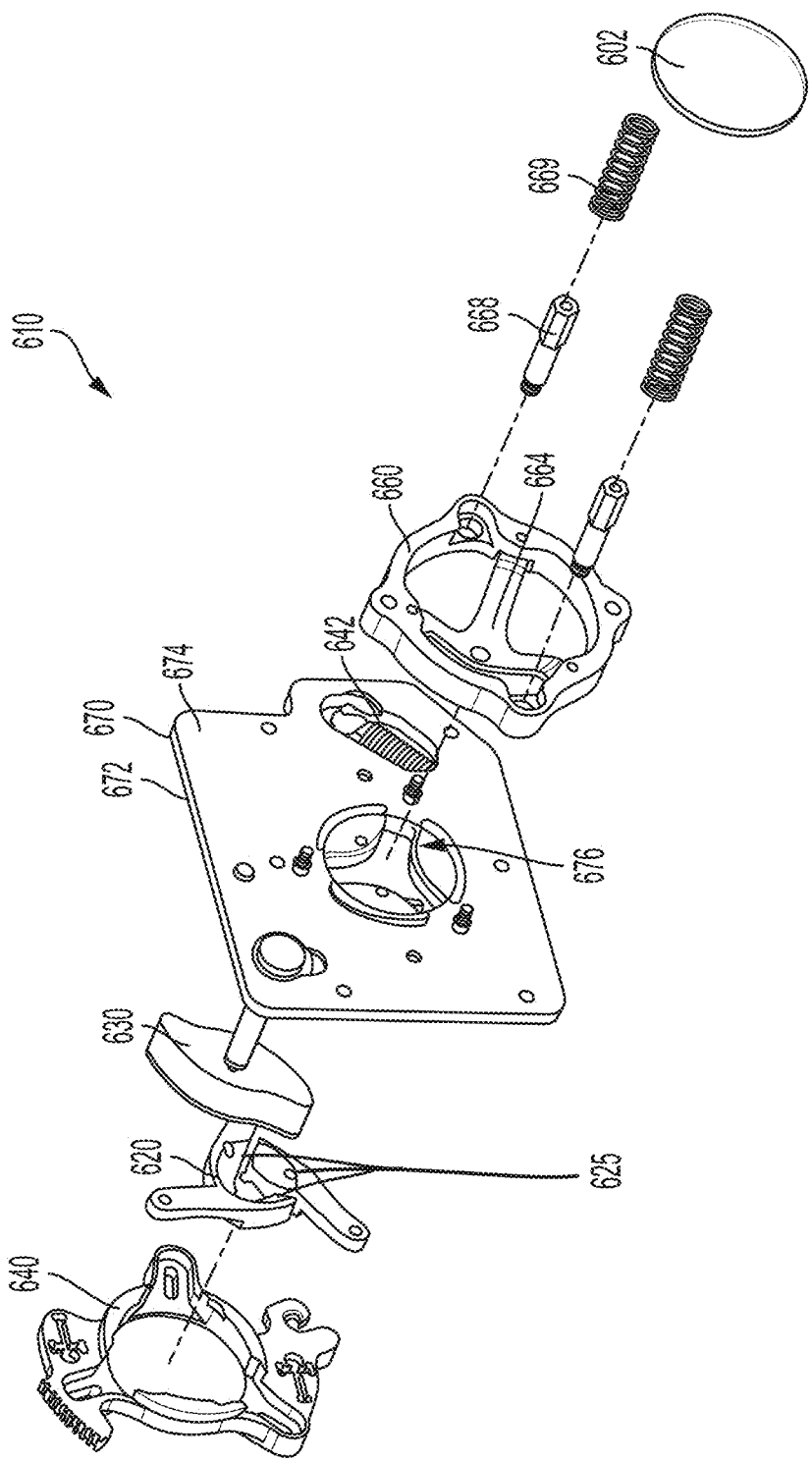
FIG. 10 shows the assembly of a receptacle according to some embodiments.

FIG. 10 shows an exploded view of a receptacle 610 according to some embodiments. The receptacle 610 may be included in illuminators such as illuminator 100 as shown in FIG. 1. The receptacle 610 may include similar features to those previously described such as a plurality of clamping jaws 620, a locking guide 640, a clutch 660, a user-operated actuator 630, and a base plate 670. For simplicity, the similar features will not be described in detail for receptacle 610.

According to some embodiments, a central portion 664 of the clutch 660 may be shaped such that a lens 602 may focus light travelling within the illuminator onto a connector (such as connector 122) positioned between the clamping jaws 620 without requiring a light pipe. According to some embodiments, the central portion 664 may have a conical shape.

According to some embodiments, the base plate 670 has a shaped aperture 676 whose shape corresponds with the shape of the central portion 664 of the clutch 660. According to some embodiments, bottom surfaces of the clamping jaws 620 may include recessed conical portions 625 that are shaped such that the central portion 664 does not collide with the bottom surfaces of the clamping jaws 620 when the receptacle is assembled onto the base plate 670.

Figure 11A:
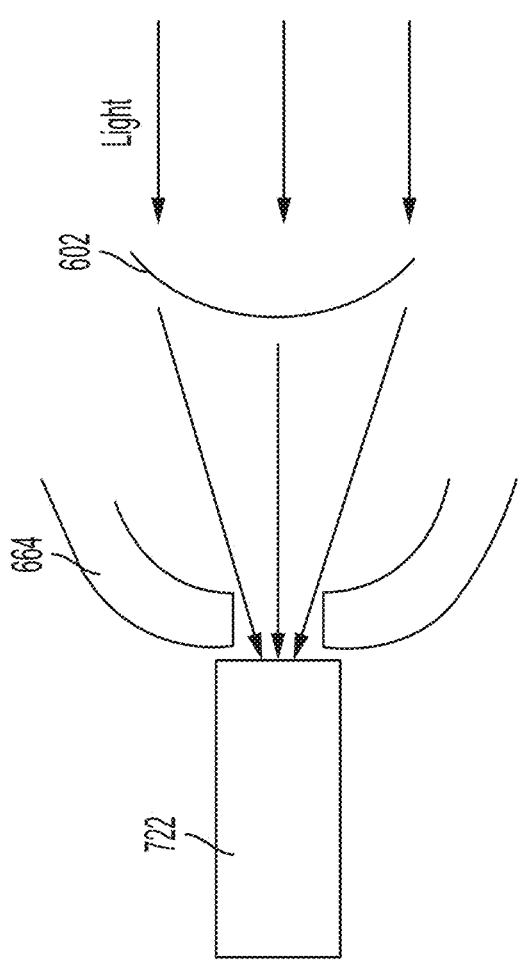
FIGS. 11A and 11B schematically show a light pathway from an illuminator to the fibers of a connector.

According to some embodiments, for example as shown schematically in FIG. 11A, light may be focused directly from lens 602 to the connector (such as connector 122 or connector 722 shown schematically in FIG. 11A) through the central portion 664. Focusing light directly to the gripped connector 722 eliminates power loss associated with use of a light pipe.

Figure 11B:
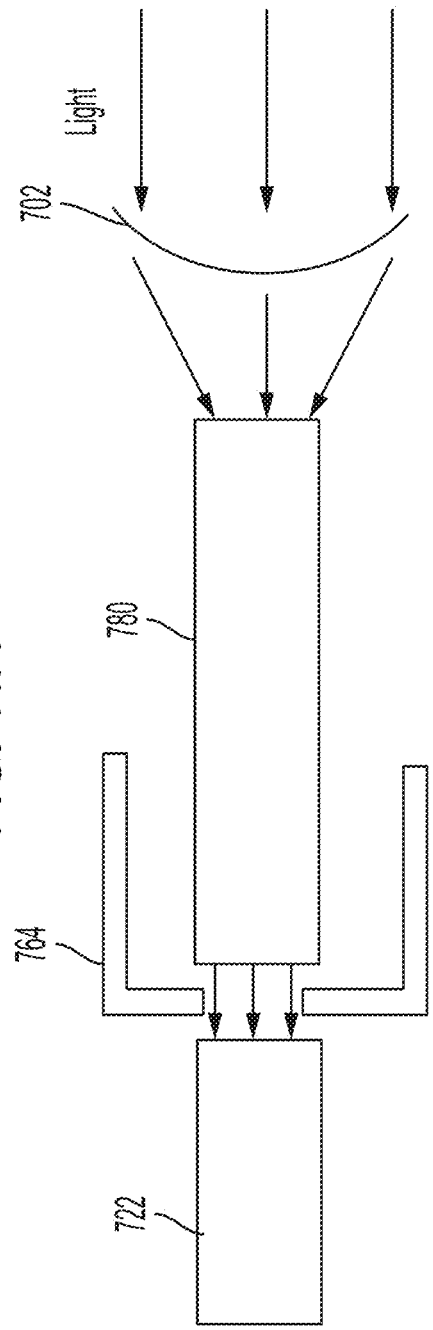

FIG. 11B shows an example of how light may be focused to the light pipe such that the light travels through the light pipe and to the connector 122 of FIG. 4. According to some embodiments, the central portion 764 of a clutch (such as clutch 160) may include a light pipe 780 such that lens 702 focuses light onto the light pipe 780 which allows the light to travel to the connector 722.

FIG. 12 shows an exemplary endoscopic imaging system 10, including a scope assembly 11 which may be utilized in endoscopic procedures. The scope assembly 11 incorporates an endoscope or scope 12 which is coupled to a camera head 16 by a coupler 13 located at the distal end of the camera head 16. According to some embodiments, the endoscope 12 can be the endoscope 101 of FIG. 1. Light is provided to the scope 12 by an illuminator 14 via a light guide 26, such as a fiber optic cable. According to some embodiments, the illuminator 14 can be illuminator 100 of FIG. 1. According to some embodiments, the light cable 26 can be the light cable 120 of FIG. 1. The camera head 16 is coupled to a camera control unit (CCU) 18 by an electrical cable 15. The CCU 18 is preferably connected to, and communicates with, the light source 14. Operation of the camera 16 is controlled, in part, by the CCU 18. The cable 15 conveys video image data from the camera head 16 to the CCU 18 and conveys various control signals bidirectionally between the camera head 16 and the CCU 18. According to some embodiments, the image data output by the camera head 16 is digital.

According to some embodiments, a control or switch arrangement 17 is provided on the camera head 16 and allows a user to manually control various functions of the system 10. According to some embodiments, voice commands are input into a microphone 25 mounted on a headset 27 worn by the surgeon and coupled to a voice-control unit 23. A hand-held control device 21, such as a tablet with a touch screen user interface or a PDA, may be coupled to the voice control unit 23 as a further control interface. According to some embodiments, a recorder 31 and a printer 33 may be coupled to the CCU 18. According to some embodiments, additional devices, such as an image capture and archiving device, may be included in the system 10 and coupled to the CCU 18. According to some embodiments, video image data acquired by the camera head 16 and processed by the CCU 18 is converted to images, which can be displayed on a monitor 20, recorded by the recorder 31, and/or used to generate static images, hard copies of which can be produced by the printer 33.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. An illuminator comprising a receptacle for connecting a light cable to an illuminator, the receptacle comprising:
a clamp assembly comprising a plurality of clamping jaws that are moveable by the clamp assembly from an open configuration in which a connecter of the light cable can be positioned between the clamping jaws for receiving light traveling in a light pathway in the illuminator to a closed configuration in which the clamping jaws completely block the light pathway; and
a clutch that is movable between an engaged position in which the clutch engages the clamp assembly for holding the clamping jaws in the open configuration and a disengaged position in which the clutch is disengaged from the clamp assembly for allowing the clamping jaws to move to a gripped configuration in which the clamping jaws grip onto the connector positioned between the clamping jaws and to the closed configuration, the clutch comprising a central portion that can be pushed by the connector when the connector is positioned between the clamping jaws to move the clutch out of the engaged position so that the clamp assembly moves the clamping jaws to the gripped configuration.

2. The illuminator of claim 1, wherein the clamp assembly comprises a locking guide operatively connected to each clamping jaw of the plurality of clamping jaws, the locking guide configured for moving between a first position for holding the clamping jaws in the open configuration and a second position for holding the jaws in the closed configuration.

3. The illuminator of claim 1, wherein the receptacle comprises a user-operated actuator operatively connected to the clamp assembly for moving the clamping jaws from the closed configuration to the open configuration.

4. The illuminator of claim 1, wherein each clamping jaw of the plurality of clamping jaws comprises a recessed portion adjacent to an overlapping portion so that in the closed configuration, the overlapping portion of each clamping jaw extends over the recessed portion of at least another clamping jaw of the plurality of clamping jaws.

5. The illuminator of claim 1 comprising a base plate comprising a first side and a second side opposite to the first side, wherein a plurality of protrusions of the clutch extend from the second side of the base plate to the first side of the base plate when the clutch is in the engaged position.

6. The illuminator of claim 1, wherein the plurality of clamping jaws comprises a plurality of inwardly facing gripping surfaces that are outwardly spaced from the central portion of the clutch when the clutch is in the engaged position.

7. The illuminator of claim 1, wherein the central portion of the clutch extends between the plurality of clamping jaws when the clutch is in the engaged position.

8. The illuminator of claim 1, wherein the clutch is configured to move translationally between the engaged position and the disengaged position in a direction orthogonal to a movement of the plurality of clamping jaws between the open configuration and the closed configuration.

9. The illuminator of claim 1 comprising a base plate, wherein the clamp assembly is positioned on a first side of the base plate and the clutch is positioned on a second side of the base plate that is opposite the first side of the base plate.

10. The illuminator of claim 9, wherein the clutch comprises a plurality of protrusions that extend between the second side of the base plate and the first side of the base plate for holding the locking guide in the first position.

11. The illuminator of claim 1 comprising a base plate for supporting the receptacle, wherein the central portion of the clutch fits into an aperture in the base plate.

12. The illuminator of claim 1, wherein the receptacle is configured to receive connectors having a range of diameters.

13. The illuminator of claim 1, wherein the connector of the light cable is for an endoscope.

14. The illuminator of claim 1, wherein the illuminator is configured to provide illuminating light to an endoscope via the light cable.

15. The illuminator of claim 1, wherein the illuminator comprises the light cable.

16. The illuminator of claim 1 comprising a lens for focusing light travelling in the light pathway to the central portion of the clutch.

17. The illuminator of claim 1 comprising a light pipe located in the central portion of the clutch.

18. The illuminator of claim 1, wherein the central portion of the clutch extends between an aperture of a base plate when the clutch is in the engaged position and in the disengaged position.

19. The illuminator of claim 1 comprising one or more guide posts that support the clutch between a back plate and a base plate.

20. The illuminator of claim 19, wherein the clutch comprises rolling pins configured to interface the one or more guide posts for reducing friction during clutch movement between the engaged position and the disengaged position with the clamp assembly.

21. The illuminator of claim 19, wherein the one or more guide posts comprise a hard stop that limits clutch movement between the engaged position and the disengaged position with the clamp assembly.

22. An illuminator comprising a receptacle for connecting a light cable to an illuminator, the receptacle comprising:
  a plurality of clamping jaws; and
  a locking guide operatively connected to each clamping jaw of the plurality of clamping jaws and configured for rotating about a light pathway between a first rotational position for holding the clamping jaws in an open configuration in which a connecter of the light cable can be positioned between the clamping jaws for receiving light traveling in the light pathway in the illuminator and a second rotational position for holding the clamping jaws in a closed configuration in which the clamping jaws completely block the light pathway; and
  wherein each clamping jaw of the plurality of clamping jaws comprises at least one protrusion that slideably engages a respective slot in the locking guide for operatively connecting each clamping jaw of the plurality of clamping jaws to the locking guide.

23. The illuminator of claim 22, wherein the clamping jaws are moveable to a gripped configuration in which the clamping jaws grip onto the connector positioned between the clamping jaws.

24. The illuminator of claim 22, wherein each clamping jaw of the plurality of clamping jaws comprises a recessed portion adjacent to an overlapping portion so that in the closed configuration, the overlapping portion of each clamping jaw extends over the recessed portion of at least another clamping jaw of the plurality of clamping jaws.

25. The illuminator of claim 22, wherein the receptacle comprises a user-operated actuator operatively connected to the locking guide for moving the locking guide from the second position to the first position.

26. The illuminator of claim 22, wherein the locking guide is configured to automatically move the clamping jaws to the closed configuration when the gripped connector is removed from between the clamping jaws.

27. The illuminator of claim 22, wherein the locking guide is moveable to a third position for holding the clamping jaws in a gripped configuration in which the clamping jaws grip onto the connector positioned between the clamping jaws.

28. The illuminator of claim 22 comprising a clutch that is movable between an engaged position in which the clutch holds the locking guide in the first position and a disengaged position in which the clutch is disengaged from the locking guide for allowing the locking guide to move to the second position and to a third position, wherein the locking guide in the third position holds the clamping jaws in a gripped configuration in which the clamping jaws grip onto the connector positioned between the clamping jaws.

29. The illuminator of claim 28, wherein the locking guide comprises rolling pins configured to interface the clutch for reducing friction during clutch movement between the engaged position and the disengaged position with the locking guide.

30. The illuminator of claim 22, wherein the locking guide is spring loaded via a spring that attaches the locking guide to a base plate via machined hooks in the base plate.

31. The illuminator of claim 22, wherein the locking guide is spring loaded via a spring that attaches the locking guide to a base plate via machined apertures in the base plate.

32. The illuminator of claim 22, wherein the locking guide is spring loaded via a spring that attaches the locking guide to a base plate via machined hooks in the locking guide.

33. The illuminator of claim 22, wherein the locking guide is spring loaded via a spring that attaches the locking guide to a base plate via machined apertures in the locking guide.

34. An illuminator comprising a receptacle for connecting a light cable to an illuminator, the receptacle comprising:
  a plurality of clamping jaws that are moveable from an open configuration in which a connecter of the light cable can be positioned between the jaws for receiving light traveling in a light pathway in the illuminator to a closed configuration in which the clamping jaws completely block the light pathway;
  a locking guide operatively connected to the plurality of clamping jaws for moving the plurality of clamping jaws between the open configuration and the closed configuration, the locking guide being moveable between a first position configured for holding the clamping jaws in the open configuration, a second position configured for holding the clamping jaws in the closed configuration, and a third position configured for holding the clamping jaws in a gripped configuration in which the clamping jaws grip onto the connector positioned between the clamping jaws; and a clutch that is movable between an engaged position for holding the locking guide in the first position and a disengaged position for allowing the locking guide to move to the second position and to the third position, the clutch comprising a central portion that can be pushed by the connector when the connector is positioned between the jaws to move the clutch out of the engaged position so that the locking guide moves the clamping jaws to the gripped configuration, wherein the locking guide is configured to automatically move the clamping jaws to the closed configuration when the gripped connector is removed from between the clamping jaws.

35. A method for connecting a receptacle of an illuminator to a light cable, the method comprising:

using a locking guide in a first position to hold a plurality of clamping jaws in an open configuration, wherein the locking guide is operatively connected to each clamping jaw of the plurality of clamping jaws;

holding the locking guide in the first position via a clutch engaged with the locking guide;

positioning a connector of the light cable between the clamping jaws in the open configuration;

pushing the connector positioned between the jaws against a central portion of the clutch to disengage the clutch from the locking guide;

gripping the inserted connector positioned between the clamping jaws; and automatically moving the clamping jaws to the closed configuration in response to removing the gripped connector from between the clamping jaws.

36. The method of claim 35, wherein gripping the inserted connector positioned between the clamping jaws comprises moving the clamping jaws to a gripped configuration.

37. The method of claim 35, wherein automatically moving the clamping jaws comprises automatically moving the locking guide to a second position that holds the clamping jaws in the closed configuration.

38. The method of claim 35, wherein automatically moving the clamping jaws comprises maintaining the clutch in the disengaged position.

39. The method of claim 35, wherein gripping the inserted connector comprises moving the locking guide from the first position in which the locking guide holds the clamping jaws in the open configuration to a second position in which the locking guide holds the clamping jaws in the gripped configuration.

* * * * *